United States Patent
Markson et al.

(10) Patent No.: US 10,896,048 B1
(45) Date of Patent: Jan. 19, 2021

(54) SYSTEMS AND METHODS FOR USER INTERFACE ADAPTATION FOR PER-USER METRICS

(71) Applicant: Express Scripts Strategic Development, Inc., St. Louis, MO (US)

(72) Inventors: Christopher R. Markson, Hawthorne, NJ (US); Pritesh J. Shah, Paramus, NJ (US); Christopher G. Lehmuth, St. Louis, MO (US)

(73) Assignee: Express Scripts Strategie Development, Inc., St. Louis, MO (US)

( * ) Notice: Subject to any disclaimer, the term of this patent is extended or adjusted under 35 U.S.C. 154(b) by 240 days.

(21) Appl. No.: 16/117,140

(22) Filed: Aug. 30, 2018

(51) Int. Cl.
| | |
|---|---|
| *G06F 7/02* | (2006.01) |
| *G06F 16/00* | (2019.01) |
| *G06F 9/451* | (2018.01) |
| *G16H 40/67* | (2018.01) |
| *G06F 17/11* | (2006.01) |
| *G06Q 10/08* | (2012.01) |
| *G16H 70/40* | (2018.01) |
| *G06N 20/00* | (2019.01) |

(52) U.S. Cl.
CPC .............. *G06F 9/451* (2018.02); *G06F 17/11* (2013.01); *G06N 20/00* (2019.01); *G06Q 10/0834* (2013.01); *G16H 40/67* (2018.01); *G16H 70/40* (2018.01)

(58) Field of Classification Search
CPC .. G06F 9/451; G06F 16/24575; G06F 16/252; G06F 16/00; G16H 40/67; G16H 70/40; G06N 20/00; G06Q 10/0834
See application file for complete search history.

(56) References Cited

U.S. PATENT DOCUMENTS

| | | | |
|---|---|---|---|
| 6,430,430 B1 | 8/2002 | Gosche | |
| 7,380,213 B2 | 5/2008 | Pokorny et al. | |
| 8,429,103 B1 | 4/2013 | Aradhye et al. | |
| 8,510,238 B1 | 8/2013 | Aradhye et al. | |
| 2005/0060199 A1* | 3/2005 | Siegel | G16H 40/67 705/2 |
| 2008/0195422 A1* | 8/2008 | Nessinger | G06Q 50/22 705/3 |
| 2009/0319456 A1 | 12/2009 | Consul et al. | |
| 2011/0051992 A1 | 3/2011 | Cobb et al. | |

(Continued)

*Primary Examiner* — Bruce M Moser
(74) *Attorney, Agent, or Firm* — Harness, Dickey & Pierce, PLC

(57) ABSTRACT

A computer system for dynamic adaptation of a user interface according to data store mining includes a data store configured to index event data of a plurality of events. A data analyst device is configured to render the user interface to a data analyst and transmit a message that identifies a selected identifier of the plurality of identifiers. A data processing circuit is configured to train a machine learning model based on event data stored by the data store for a first set of identifiers from within a predetermined epoch. An interface circuit determines an interface metric for the selected identifier based on the determined output of the selected identifier and transmits the interface metric to the data analyst device. The data analyst device is configured to, in response to the interface metric from the interface circuit, selectively perform a modification or removal of a second user interface element.

18 Claims, 9 Drawing Sheets

(56) References Cited

U.S. PATENT DOCUMENTS

| | | | | |
|---|---|---|---|---|
| 2011/0152830 A1* | 6/2011 | Ruchti | ............... | G16H 20/17 |
| | | | | 604/504 |
| 2016/0210427 A1* | 7/2016 | Mynhier | ............... | G16H 50/20 |
| 2016/0292456 A1* | 10/2016 | Dubey | ............... | G06Q 10/10 |
| 2018/0089699 A1* | 3/2018 | Arniotes | ............ | G06F 11/3438 |

* cited by examiner

SYSTEMS AND METHODS FOR USER INTERFACE ADAPTATION FOR PER-USER METRICS

FIELD

The present disclosure relates to user interface adaptation and, more particularly, to determining a per-user metric to transform the user interface.

BACKGROUND

Currently, entities, such as high-volume pharmacies, offer online drug management programs. For example, a user who is a member of a pharmacy can create an account on a user device via a web portal to access the drug management program. Each user may be able to access the same information and may be presented with an identical user interface. Similarly, a support representative or an analyst working for the pharmacy may access user information that is not customized to the user or the user population.

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

A computer system for dynamic adaptation of a user interface according to data store mining is presented. The system includes a data store configured to index event data of a plurality of events. Each event of the plurality of events corresponds to a physical object being supplied to a user identified by an identifier on behalf of a first entity. The data store is configured to store descriptive data for each of a plurality of identifiers. The system also includes a data analyst device configured to render the user interface to a data analyst and to transmit a message that identifies a selected identifier of the plurality of identifiers. The user interface includes a first user interface element and a second user interface element.

The system further includes a data processing circuit configured to identify a first set of identifiers from the plurality of identifiers based on commonality among the descriptive data stored by the data store across the first set of identifiers. The data processing circuit is also configured to train a machine learning model for the first set of identifiers based on event data stored by the data store for the first set of identifiers from within a predetermined epoch. The machine learning model is trained using parallel processing of records from the data store. The parallel processing includes assigning analysis of the indexed event data of each of a subset of the first set of identifiers to respective processor threads for parallel execution on processing hardware.

The system includes an interface circuit configured to, in response to receiving the message from the data analyst device, determine an output of the selected identifier using the machine learning model from the data processing circuit. The output of the selected identifier represents an amount of resources expected to be used by the selected identifier for a second epoch subsequent to the predetermined epoch. The interface circuit is further configured to determine an interface metric for the selected identifier based on the determined output of the selected identifier and transmit the interface metric to the data analyst device. The data analyst device is configured to, in response to the interface metric from the interface circuit, selectively perform at least one of modification and removal of the second user interface element.

In other features, the interface circuit is configured to determine the interface metric for the selected identifier further based on a retention value and a population retention value. The retention value indicates a likelihood of the selected identifier being associated with the first entity for the second epoch. The population retention value indicates a likelihood of a population of identifiers encompassing the selected identifier being associated with the first entity for the second epoch. In other features, an operator of the data analyst device is one of (i) a user identified by the selected identifier, (ii) an analyst for the first entity, and (iii) a support representative of the first entity.

In other features, a high-volume pharmacy includes the computer system, and the first entity is the high-volume pharmacy. In other features, the amount of resources expected to be used by the selected identifier includes at least one of (i) an expected number of calls received from the selected identifier, (ii) an expected number of drug orders mailed to the selected identifier; and (iii) an expected measure of drugs dispensed to the selected identifier. In other features, the interface circuit is configured to, in response to receiving the message from the data analyst device, determine an intake of the selected identifier using the machine learning model from the data processing circuit. The intake of the selected identifier represents an amount of resources expected to be received by the first entity from the selected identifier for the second epoch. The interface circuit is further configured to determine the interface metric for the selected identifier based on the determined output of the selected identifier and the determined intake of the selected identifier in response to receiving the message from the data analyst device.

In other features, the amount of resources expected to be received from the selected identifier is a difference, for each event of the selected identifier, between an amount received for the event and an amount expended for the event. In other features, the data analyst device includes a persona determination module configured to transmit the message to the interface circuit, receive the interface metric of the selected identifier from the interface circuit, and identify a corresponding persona of the selected identifier based on the received interface metric of the selected identifier. In other features, the data analyst device includes a user interface adaptation module configured to transform the user interface of the data analyst device according to the corresponding persona. In other features, the corresponding persona is selected from a set of personas including at least one of: (i) a set of user personas, (ii) a set of analyst personas. (iii) a set of support personas.

In other features, the selected identifier is a population of identifiers encompassing the selected identifier. In other features, descriptive data for each of the plurality of identifiers includes at least one of: (i) name, (ii) support call logs, (iii) support chat logs; and (iv) selected identifier subscription duration. In other features, descriptive data for each of the plurality of identifiers includes population of identifiers encompassing the selected identifier subscription duration. In other features, the event data includes at least one of, for each event (i) a respective intake and (ii) a respective output. In other features, the interface circuit includes an actual retention module configured to identify a population of identifiers encompassing the selected identifier, determine a previous retention value of the selected identifier based on a duration of presence of the selected identifier within the identified population during the predetermined epoch, and determine a previous population retention value of the identified population based on a duration of presence of the identified population as a client of the first entity during the predetermined epoch.

In other features, the interface circuit calculates the interface metric according to an equation. The equation is:

$$PUM_k = A_k \sum_{i=1}^{n} \frac{G_i(M_k - C_k)r^i}{(1+d)^i},$$

where $PUM_k$ is the interface metric of the selected identifier, $A_k$ is a starting retention age of the selected identifier, n is a length of the second epoch in years, $G_i$ is an estimate of a retention value of the selected identifier at year i of the second epoch, $M_k$ is an estimated intake of the selected identifier for the second epoch, $C_k$ is the determined output of the selected identifier, r is an annual population retention value; and d is a predetermined discount rate. In other features, the length of the second epoch in years is an integer greater than or equal to one, the estimate of the retention value is less than or equal to zero, the annual population retention value is less than or equal to one; and the predetermined discount rate is greater than or equal to zero and less than one. In other features, the second user interface element indicates a shipping option of a drug. In other features, the at least one of modification and removal of the second user interface element includes, based on the interface metric, updating the shipping option of the drug to an expedited shipping option.

Further areas of applicability of the present disclosure will become apparent from the detailed description, the claims, and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings.

In the drawings, reference numbers may be reused to identify similar and/or identical elements.

DETAILED DESCRIPTION

Introduction

Adapting a user interface based on a per-user metric provides a personalized user interface, including personalized options and benefits, directly to a user. In various implementations, user interface adaptation based on the per-user metric can also be provided to support representatives and analysts when using their respective devices. The per-user metric is determined based on data stored in a storage device of a pharmacy for example, member data and claims data stored in the storage device of the pharmacy.

In various implementations, the per-user metric can be determined based on an expected user retention, an expected population retention, an expected output of the user, and an expected intake of the user. For example, the expected user retention not only considers the expected user retention with the pharmacy, but also considers the expected user retention within the user population for example, the user's employer.

Additionally, to determine the other features used to determine the per-user metric, a training group of available member claims and claims data can be analyzed to determined expected future values. For example, to anticipate the expected population retention, a likelihood of retention is calculated based on historical retention rates. Similarly, the expected output and intake are calculated based on historical outputs and intakes.

Once determined, the per-user metric is used to customize the user interface displayed to the user, an analyst, and/or a support representative. For example, based on the per-user metric, a corresponding persona is selected for display to the user at the user device. Based on the selected persona, the user interface is transformed to encourage that user's retention and to increase that user's per-user metric. In various implementations, the expected user retention is an additional factor considered when transforming the user interface.

For the analyst, the user interface may be transformed according to a persona corresponding to the analyzed user or user population's per-user metric. Additionally, for analyst purposes, the per-user metric may be displayed along with analytics related to the user or user population being analyzed. For the support representative, the user interface may transform according to the user persona and provide the support representative with available options to offer the user.

High-Volume Pharmacy

Figure 1:
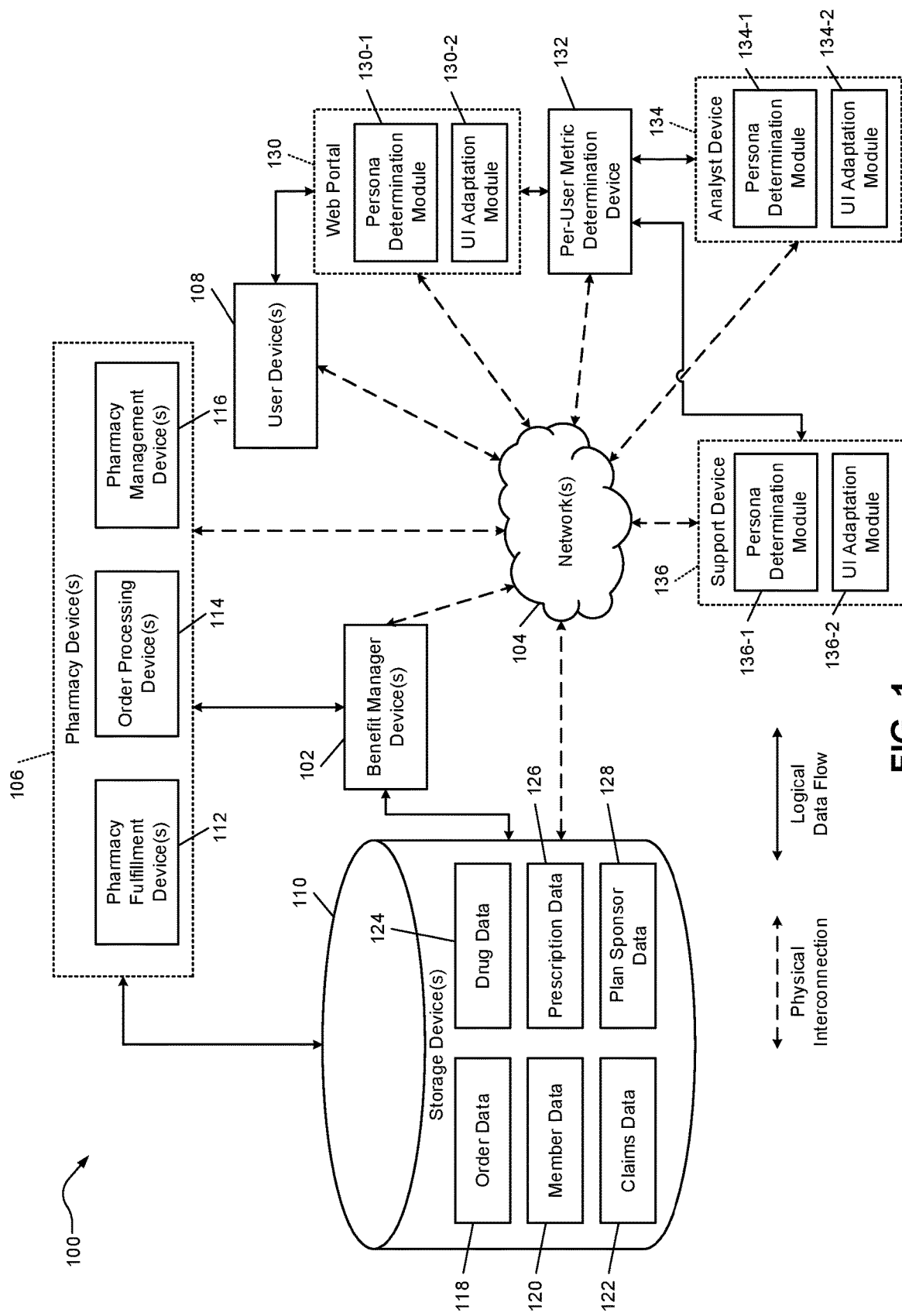
FIG. 1 is a functional block diagram of an example system including a high-volume pharmacy.

FIG. 1 is a block diagram of an example implementation of a system 100 for a high-volume pharmacy. While the system 100 is generally described as being deployed in a high-volume pharmacy or a fulfillment center (for example, a mail order pharmacy, a direct delivery pharmacy, etc.), the system 100 and/or components of the system 100 may otherwise be deployed (for example, in a lower-volume pharmacy, etc.). A high-volume pharmacy may be a pharmacy that is capable of filling at least some prescriptions mechanically. The system 100 may include a benefit manager device 102 and a pharmacy device 106 in communication with each other directly and/or over a network 104. The system 100 may also include a storage device 110.

The benefit manager device 102 is a device operated by an entity that is at least partially responsible for creation and/or management of the pharmacy or drug benefit. While the entity operating the benefit manager device 102 is typically a pharmacy benefit manager (PBM), other entities may operate the benefit manager device 102 on behalf of themselves or other entities (such as PBMs). For example, the benefit manager device 102 may be operated by a health plan, a retail pharmacy chain, a drug wholesaler, a data analytics or other type of software-related company, etc. In some implementations, a PBM that provides the pharmacy benefit may provide one or more additional benefits including a medical or health benefit, a dental benefit, a vision benefit, a wellness benefit, a radiology benefit, a pet care benefit, an insurance benefit, a long term care benefit, a nursing home benefit, etc. The PBM may, in addition to its PBM operations, operate one or more pharmacies. The pharmacies may be retail pharmacies, mail order pharmacies, etc.

Some of the operations of the PBM that operates the benefit manager device 102 may include the following activities and processes. A member (or a person on behalf of the member) of a pharmacy benefit plan may obtain a prescription drug at a retail pharmacy location (e.g., a location of a physical store) from a pharmacist or a pharmacist technician. The member may also obtain the prescription drug through mail order drug delivery from a mail order pharmacy location, such as the system 100. In some implementations, the member may obtain the prescription drug directly or indirectly through the use of a machine, such as a kiosk, a vending unit, a mobile electronic device, or a different type of mechanical device, electrical device, electronic communication device, and/or computing device. Such a machine may be filled with the prescription drug in prescription packaging, which may include multiple prescription components, by the system 100. The pharmacy benefit plan is administered by or through the benefit manager device 102.

The member may have a copayment for the prescription drug that reflects an amount of money that the member is responsible to pay the pharmacy for the prescription drug. The money paid by the member to the pharmacy may come from, as examples, personal funds of the member, a health savings account (HSA) of the member or the member's family, a health reimbursement arrangement (HRA) of the member or the member's family, or a flexible spending account (FSA) of the member or the member's family. In some instances, an employer of the member may directly or indirectly fund or reimburse the member for the copayments.

The amount of the copayment required by the member may vary across different pharmacy benefit plans having different plan sponsors or clients and/or for different prescription drugs. The member's copayment may be a flat copayment (in one example, $10), coinsurance (in one example, 10%), and/or a deductible (for example, responsibility for the first $500 of annual prescription drug expense, etc.) for certain prescription drugs, certain types and/or classes of prescription drugs, and/or all prescription drugs. The copayment may be stored in the storage device 110 or determined by the benefit manager device 102.

In some instances, the member may not pay the copayment or may only pay a portion of the copayment for the prescription drug. For example, if a usual and customary cost for a generic version of a prescription drug is $4, and the member's flat copayment is $20 for the prescription drug, the member may only need to pay $4 to receive the prescription drug. In another example involving a worker's compensation claim, no copayment may be due by the member for the prescription drug.

In addition, copayments may also vary based on different delivery channels for the prescription drug. For example, the copayment for receiving the prescription drug from a mail order pharmacy location may be less than the copayment for receiving the prescription drug from a retail pharmacy location.

In conjunction with receiving a copayment (if any) from the member and dispensing the prescription drug to the member, the pharmacy submits a claim to the PBM for the prescription drug. After receiving the claim, the PBM (such as by using the benefit manager device 102) may perform certain adjudication operations including verifying eligibility for the member, identifying/reviewing an applicable formulary for the member to determine any appropriate copayment, coinsurance, and deductible for the prescription drug, and performing a drug utilization review (DUR) for the member. Further, the PBM may provide a response to the pharmacy (for example, the pharmacy system 100) following performance of at least some of the aforementioned operations.

As part of the adjudication, a plan sponsor (or the PBM on behalf of the plan sponsor) ultimately reimburses the pharmacy for filling the prescription drug when the prescription drug was successfully adjudicated. The aforementioned adjudication operations generally occur before the copayment is received and the prescription drug is dispensed. However in some instances, these operations may occur simultaneously, substantially simultaneously, or in a different order. In addition, more or fewer adjudication operations may be performed as at least part of the adjudication process.

The amount of reimbursement paid to the pharmacy by a plan sponsor and/or money paid by the member may be determined at least partially based on types of pharmacy networks in which the pharmacy is included. In some implementations, the amount may also be determined based on other factors. For example, if the member pays the pharmacy for the prescription drug without using the prescription or drug benefit provided by the PBM, the amount of money paid by the member may be higher than when the member uses the prescription or drug benefit. In some implementations, the amount of money received by the pharmacy for dispensing the prescription drug and for the prescription drug itself may be higher than when the member uses the prescription or drug benefit. Some or all of the foregoing operations may be performed by executing instructions stored in the benefit manager device 102 and/or an additional device.

Examples of the network 104 include a Global System for Mobile Communications (GSM) network, a code division multiple access (CDMA) network, 3rd Generation Partnership Project (3GPP), an Internet Protocol (IP) network, a Wireless Application Protocol (WAP) network, or an IEEE 802.11 standards network, as well as various combinations of the above networks. The network 104 may include an optical network. The network 104 may be a local area network or a global communication network, such as the Internet. In some implementations, the network 104 may include a network dedicated to prescription orders: a prescribing network such as the electronic prescribing network operated by Surescripts of Arlington, Va.

Moreover, although the system shows a single network 104, multiple networks can be used. The multiple networks may communicate in series and/or parallel with each other to link the devices 102-110.

The pharmacy device 106 may be a device associated with a retail pharmacy location (e.g., an exclusive pharmacy location, a grocery store with a retail pharmacy, or a general sales store with a retail pharmacy) or other type of pharmacy location at which a member attempts to obtain a prescription. The pharmacy may use the pharmacy device 106 to submit the claim to the PBM for adjudication.

Additionally, in some implementations, the pharmacy device 106 may enable information exchange between the pharmacy and the PBM. For example, this may allow the sharing of member information such as drug history that may allow the pharmacy to better service a member (for example, by providing more informed therapy consultation and drug interaction information). In some implementations, the benefit manager device 102 may track prescription drug fulfillment and/or other information for users that are not members, or have not identified themselves as members, at the time (or in conjunction with the time) in which they seek to have a prescription filled at a pharmacy.

The pharmacy device 106 may include a pharmacy fulfillment device 112, an order processing device 114, and a pharmacy management device 116 in communication with each other directly and/or over the network 104. The order processing device 114 may receive information regarding filling prescriptions and may direct an order component to one or more devices of the pharmacy fulfillment device 112 at a pharmacy. The pharmacy fulfillment device 112 may fulfill, dispense, aggregate, and/or pack the order components of the prescription drugs in accordance with one or more prescription orders directed by the order processing device 114.

In general, the order processing device 114 is a device located within or otherwise associated with the pharmacy to enable the pharmacy fulfilment device 112 to fulfill a prescription and dispense prescription drugs. In some implementations, the order processing device 114 may be an external order processing device separate from the pharmacy and in communication with other devices located within the pharmacy.

For example, the external order processing device may communicate with an internal pharmacy order processing device and/or other devices located within the system 100. In some implementations, the external order processing device may have limited functionality (e.g., as operated by a user requesting fulfillment of a prescription drug), while the internal pharmacy order processing device may have greater functionality (e.g., as operated by a pharmacist).

The order processing device 114 may track the prescription order as it is fulfilled by the pharmacy fulfillment device 112. The prescription order may include one or more prescription drugs to be filled by the pharmacy. The order processing device 114 may make pharmacy routing decisions and/or order consolidation decisions for the particular prescription order. The pharmacy routing decisions include what device(s) in the pharmacy are responsible for filling or otherwise handling certain portions of the prescription order. The order consolidation decisions include whether portions of one prescription order or multiple prescription orders should be shipped together for a user or a user family. The order processing device 114 may also track and/or schedule literature or paperwork associated with each prescription order or multiple prescription orders that are being shipped together. In some implementations, the order processing device 114 may operate in combination with the pharmacy management device 116.

The order processing device 114 may include circuitry, a processor, a memory to store data and instructions, and communication functionality. The order processing device 114 is dedicated to performing processes, methods, and/or instructions described in this application. Other types of electronic devices may also be used that are specifically configured to implement the processes, methods, and/or instructions described in further detail below.

In some implementations, at least some functionality of the order processing device 114 may be included in the pharmacy management device 116. The order processing device 114 may be in a client-server relationship with the pharmacy management device 116, in a peer-to-peer relationship with the pharmacy management device 116, or in a different type of relationship with the pharmacy management device 116. The order processing device 114 and/or the pharmacy management device 116 may communicate directly (for example, such as by using a local storage) and/or through the network 104 (such as by using a cloud storage configuration, software as a service, etc.) with the storage device 110.

The storage device 110 may include: non-transitory storage (for example, memory, hard disk, CD-ROM, etc.) in communication with the benefit manager device 102 and/or the pharmacy device 106 directly and/or over the network 104. The non-transitory storage may store order data 118, member data 120, claims data 122, drug data 124, prescription data 126, and/or plan sponsor data 128. Further, the system 100 may include additional devices, which may communicate with each other directly or over the network 104.

The order data 118 may be related to a prescription order. The order data may include type of the prescription drug (for example, drug name and strength) and quantity of the prescription drug. The order data 118 may also include data used for completion of the prescription, such as prescription materials. In general, prescription materials include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, etc. The order data 118 may be used by a high-volume fulfillment center to fulfill a pharmacy order.

In some implementations, the order data 118 includes verification information associated with fulfillment of the prescription in the pharmacy. For example, the order data 118 may include videos and/or images taken of (i) the prescription drug prior to dispensing, during dispensing, and/or after dispensing, (ii) the prescription container (for example, a prescription container and sealing lid, prescription packaging, etc.) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other types of verification information such as barcode data read from pallets, bins, trays, or carts used to transport prescriptions within the pharmacy may also be stored as order data 118.

The member data 120 includes information regarding the members associated with the PBM. The information stored as member data 120 may include personal information, personal health information, protected health information, etc. Examples of the member data 120 include name, address, telephone number, e-mail address, prescription drug history, etc. The member data 120 may include a plan sponsor identifier that identifies the plan sponsor associated with the member and/or a member identifier that identifies the member to the plan sponsor. The member data 120 may include a member identifier that identifies the plan sponsor associated with the user and/or a user identifier that identifies the user to the plan sponsor. The member data 120 may also include dispensation preferences such as type of label, type of cap, message preferences, language preferences, etc.

The member data 120 may be accessed by various devices in the pharmacy (for example, the high-volume fulfillment center, etc.) to obtain information used for fulfillment and shipping of prescription orders. In some implementations, an external order processing device operated by or on behalf of a member may have access to at least a portion of the member data 120 for review, verification, or other purposes.

In some implementations, the member data 120 may include information for persons who are users of the pharmacy but are not members in the pharmacy benefit plan being provided by the PBM. For example, these users may obtain drugs directly from the pharmacy, through a private label service offered by the pharmacy, the high-volume fulfillment center, or otherwise. In general, the use of the terms "member" and "user" may be used interchangeably.

The claims data 122 includes information regarding pharmacy claims adjudicated by the PBM under a drug benefit program provided by the PBM for one or more plan sponsors. In general, the claims data 122 includes an identification of the client that sponsors the drug benefit program under which the claim is made, and/or the member that purchased the prescription drug giving rise to the claim, the prescription drug that was filled by the pharmacy (e.g., the national drug code number, etc.), the dispensing date, generic indicator, generic product identifier (GPI) number, medication class, the cost of the prescription drug provided under the drug benefit program, the copayment/coinsurance amount, rebate information, and/or member eligibility, etc. Additional information may be included.

In some implementations, other types of claims beyond prescription drug claims may be stored in the claims data 122. For example, medical claims, dental claims, wellness claims, or other types of health-care-related claims for members may be stored as a portion of the claims data 122.

In some implementations, the claims data 122 includes claims that identify the members with whom the claims are associated. Additionally or alternatively, the claims data 122 may include claims that have been de-identified (that is, associated with a unique identifier but not with a particular, identifiable member).

The drug data 124 may include drug name (e.g., technical name and/or common name), other names by which the drug is known, active ingredients, an image of the drug (such as in pill form), etc. The drug data 124 may include information associated with a single medication or multiple medications.

The prescription data 126 may include information regarding prescriptions that may be issued by prescribers on behalf of users, who may be members of the pharmacy benefit plan—for example, to be filled by a pharmacy. Examples of the prescription data 126 include user names, medication or treatment (such as lab tests), dosing information, etc. The prescriptions may include electronic prescriptions or paper prescriptions that have been scanned. In some implementations, the dosing information reflects a frequency of use (e.g., once a day, twice a day, before each meal, etc.) and a duration of use (e.g., a few days, a week, a few weeks, a month, etc.).

In some implementations, the order data 118 may be linked to associated member data 120, claims data 122, drug data 124, and/or prescription data 126. The plan sponsor data 128 includes information regarding the plan sponsors of the PBM. Examples of the plan sponsor data 128 include company name, company address, contact name, contact telephone number, contact e-mail address, etc.

UI Adaptation

In various implementations, the member data 120 may also include phone call or internet chat logs for each user and user population. Each log may include a duration as well as a corresponding claim that the log is referencing. The member data 120 may also include, for each user, the duration of their membership and the duration of their presence in the population. The duration of membership may include a duration of pharmacy membership, a duration of inclusion in the user population, and duration of pharmacy membership of each user population.

In various implementations, the claims data 122 may also include cost data for each member or user indicating an amount of cost the pharmacy has incurred for each user based on customer support, shipping costs, etc. The claims data 122 may also include margin data indicating an intake of the pharmacy for each claim of each user. The intake indicates an amount the pharmacy has benefited financially for each user. The output and intake may be determined over a period of time.

In various implementations, a web portal 130 includes a persona determination module 130-1 and a user interface adaptation module 130-2. The web portal 130 is in communication with the user device 108 and a per-user metric determination device 132 via the network 104. A user can create an account to manage the user prescriptions via the web portal 130. In response to the user logging on to their user account, the persona determination module 130-1 determines which persona corresponds to the user. This may prompt a per-user metric calculation (or lookup) for the user. The user interface adaptation module 130-2 receives the determined persona from the persona determination module 130-1 and transforms the user interface presented to the user for example, on the user device 108 according to the determined persona. In this way, the user interface presented to the user is personalized.

In various implementations, the persona determination module 130-1 determines the persona that corresponds to the user based on the per-user metric of the user. The persona determination module 130-1 receives the per-user metric of the user from the per-user metric determination device 132. The per-user metric determination device 132 receives relevant information of the user from the storage device 110 via the network. Based on the received relevant information, the per-user metric determination device 132 determines a retention metric of the user and a benefit metric of the user in order to determine the per-user metric. The persona determination module 130-1 then determines the persona that corresponds to the per-user metric.

In various implementations, the storage device 110 is a data store, a data warehouse, a relational database, a NoSQL database, or a data repository. The storage device 110 is configured to index event data. The event data includes member data 120 and claims data 122. The data store indexes a plurality of events, where each event corresponds to a physical object, for example, a prescription drug, being supplied to a user or patient. For example, the prescription drug can be mailed to the user, the user can obtain the prescription drug from a retail location, such as a pharmacy, etc. In the data store, and in the system, each user or patient can be identified using an identifier unique to the user/patient.

The data store can further store descriptive data corresponding to each identifier to indicate the corresponding user. For example, this descriptive data can include demographic data such as age and sex, social information such as histories of smoking and drinking, and health data such as present and past medical conditions.

The system 100 includes an analyst device 134 including a persona determination module 134-1 and a user interface adaptation module 134-2. The system 100 includes a support device 136 including a persona determination module 136-1 and a user interface adaptation module 136-2. Data analysts of the pharmacy may use the analyst device 134 to run analytics of specific users or specific user populations based on submitted parameters or selected relevant information. In various implementations, the pharmacy may analyze potential clients based on similar clients.

The analyst device 134 may include a homepage for an analyst to input a future number of years, a target user or client, and additional information related to the analysis. Based on the determined per-user metric, the personas may vary according to the analyzed data. For example, if the per-user metric is low, a corresponding persona may adapt the user interface to highlight potential areas of improvement, with respect to the per-user metric, for the user or client.

The support device 136 displays a user interface to a support representative according to a user or user population that the support representative is assisting. For example, the support representative may be at a call center and receive a call from a particular user. The support representative may identify the caller to the support device 136 if the phone system had not yet identified the caller before connecting the caller to the support representative. The persona determination module 136-1 determines a persona of the user based on the submitted parameters and displays a user interface according to the persona. The user interface adaptation module 136-2 transforms the user interface. In this way, the support representative is displayed a customized user interface according to the user or the user population of the user calling for assistance, such as the ability to expedite shipping for free or at a reduced rate.

The analyst device 134 may also be referred to as a data analyst device, where an analyst can query metrics for one or more users. The metric(s) may be displayed to the analyst, either individually or in the aggregate. In some implementations, the metric(s) may cause the user interface of the data analyst device to be updated, such as by removing a user interface element or modifying a user interface element (such as by modifying a displayed number or changing a font characteristic).

The web portal 130 may be considered a special case of the data analyst device, where a first user accessing the data analyst device is restricted to only information about the first user. Further, in the case of the web portal 130, the data analyst device may prevent display of the metric to the first user and instead only modify the user interface in response to the metric.

The support device 136 may also be considered a special case of the data analyst device, where the support representative using the data analyst device chooses one user at a time (generally, the person whom the support representative is interacting with via phone, chat, etc.). The metric for the chosen user may be displayed to the support representative. In other implementations, the metric may be used to adapt user interface elements, such as revealing or hiding buttons related to expedited shipping, or modifying text describing the cost or speed of expedited shipping. In such implementations, the metric may or may not be shown.

Fulfillment Device

Figure 2:
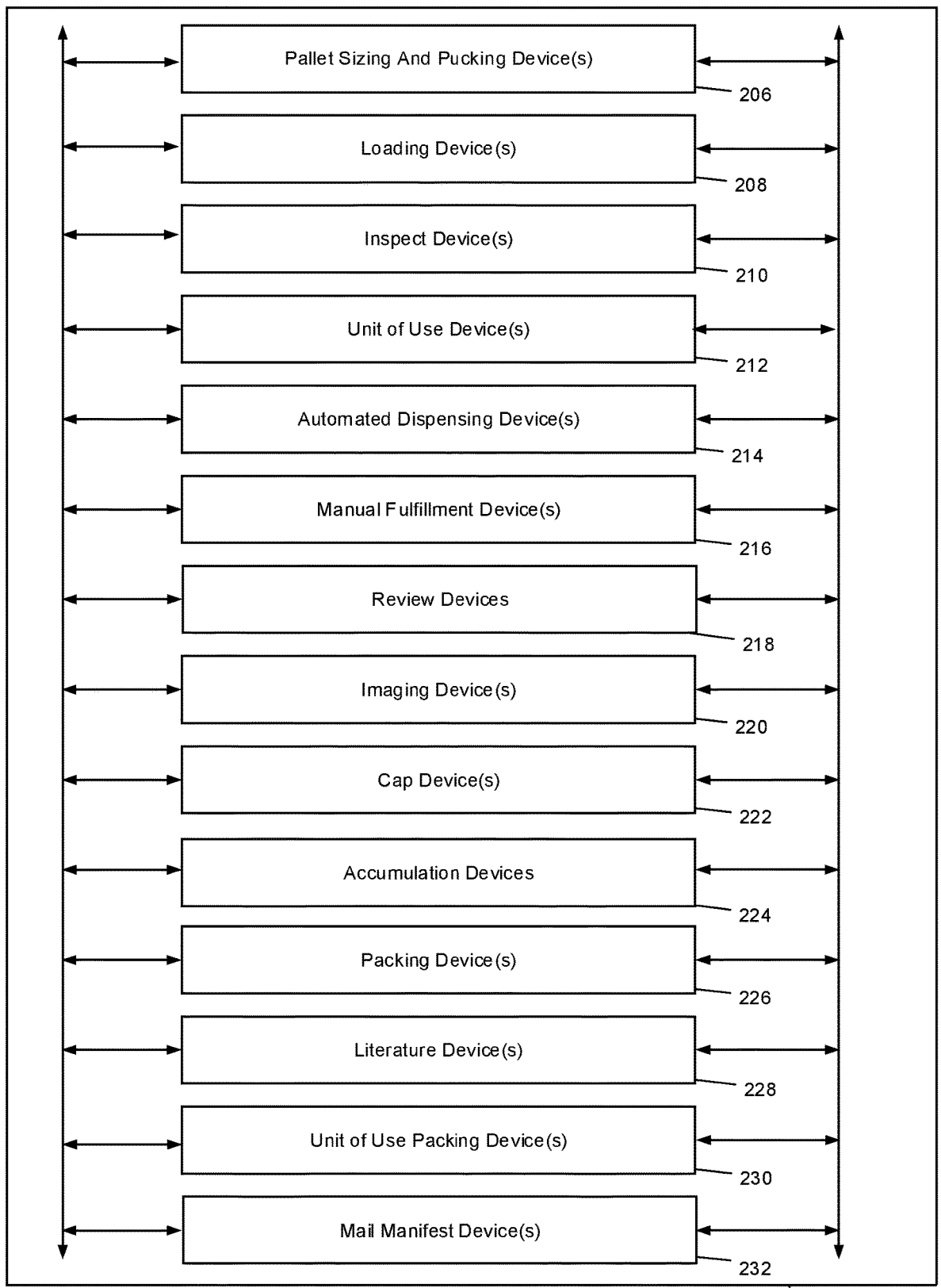
FIG. 2 is a functional block diagram of an example pharmacy fulfillment device, which may be deployed within the system of FIG. 1.

FIG. 2 illustrates the pharmacy fulfillment device 112 according to an example implementation. The pharmacy fulfillment device 112 may be used to process and fulfill prescriptions and prescription orders. After fulfillment, the fulfilled prescriptions are packed for shipping.

The pharmacy fulfillment device 112 may include devices in communication with the benefit manager device 102, the order processing device 114, and/or the storage device 110, directly or over the network 104. Specifically, the pharmacy fulfillment device 112 may include pallet sizing and pucking device(s) 206, loading device(s) 208, inspect device(s) 210, unit of use device(s) 212, automated dispensing device(s) 214, manual fulfillment device(s) 216, review devices 218, imaging device(s) 220, cap device(s) 222, accumulation devices 224, packing device(s) 226, literature device(s) 228, unit of use packing device(s) 230, and mail manifest device(s) 232. Further, the pharmacy fulfillment device 112 may include additional devices, which may communicate with each other directly or over the network 104.

In some implementations, operations performed by one of these devices 206-232 may be performed sequentially, or in parallel with the operations of another device as may be coordinated by the order processing device 114. In some implementations, the order processing device 114 tracks a prescription with the pharmacy based on operations performed by one or more of the devices 206-232.

In some implementations, the pharmacy fulfillment device 112 may transport prescription drug containers, for example, among the devices 206-232 in the high-volume fulfillment center, by use of pallets. The pallet sizing and pucking device 206 may configure pucks in a pallet. A pallet may be a transport structure for a number of prescription containers, and may include a number of cavities. A puck may be placed in one or more than one of the cavities in a pallet by the pallet sizing and pucking device 206. The puck may include a receptacle sized and shaped to receive a prescription container. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 114 based on prescriptions that the order processing device 114 decides to launch. The arrangement logic may be implemented directly in the pallet sizing and pucking device 206. Once a prescription is set to be launched, a puck suitable for the appropriate size of container for that prescription may be positioned in a pallet by a robotic arm or pickers. The pallet sizing and pucking device 206 may launch a pallet once pucks have been configured in the pallet.

The loading device 208 may load prescription containers into the pucks on a pallet by a robotic arm, a pick and place mechanism (also referred to as pickers), etc. In various implementations, the loading device 208 has robotic arms or pickers to grasp a prescription container and move it to and from a pallet or a puck. The loading device 208 may also print a label that is appropriate for a container that is to be loaded onto the pallet, and apply the label to the container. The pallet may be located on a conveyor assembly during these operations (e.g., at the high-volume fulfillment center, etc.).

The inspect device 210 may verify that containers in a pallet are correctly labeled and in the correct spot on the pallet. The inspect device 210 may scan the label on one or more containers on the pallet. Labels of containers may be scanned or imaged in full or in part by the inspect device

210. Such imaging may occur after the container has been lifted out of its puck by a robotic arm, picker, etc., or may be otherwise scanned or imaged while retained in the puck. In some implementations, images and/or video captured by the inspect device 210 may be stored in the storage device 110 as order data 118.

The unit of use device 212 may temporarily store, monitor, label, and/or dispense unit of use products. In general, unit of use products are prescription drug products that may be delivered to a user or member without being repackaged at the pharmacy. These products may include pills in a container, pills in a blister pack, inhalers, etc. Prescription drug products dispensed by the unit of use device 212 may be packaged individually or collectively for shipping, or may be shipped in combination with other prescription drugs dispensed by other devices in the high-volume fulfillment center.

At least some of the operations of the devices 206-232 may be directed by the order processing device 114. For example, the manual fulfillment device 216, the review device 218, the automated dispensing device 214, and/or the packing device 226, etc. may receive instructions provided by the order processing device 114.

The automated dispensing device 214 may include one or more devices that dispense prescription drugs or pharmaceuticals into prescription containers in accordance with one or multiple prescription orders. In general, the automated dispensing device 214 may include mechanical and electronic components with, in some implementations, software and/or logic to facilitate pharmaceutical dispensing that would otherwise be performed in a manual fashion by a pharmacist and/or pharmacist technician. For example, the automated dispensing device 214 may include high-volume fillers that fill a number of prescription drug types at a rapid rate and blister pack machines that dispense and pack drugs into a blister pack. Prescription drugs dispensed by the automated dispensing devices 214 may be packaged individually or collectively for shipping, or may be shipped in combination with other prescription drugs dispensed by other devices in the high-volume fulfillment center.

The manual fulfillment device 216 controls how prescriptions are manually fulfilled. For example, the manual fulfillment device 216 may receive or obtain a container and enable fulfillment of the container by a pharmacist or pharmacy technician. In some implementations, the manual fulfillment device 216 provides the filled container to another device in the pharmacy fulfillment devices 112 to be joined with other containers in a prescription order for a user or member.

In general, manual fulfillment may include operations at least partially performed by a pharmacist or a pharmacy technician. For example, a person may retrieve a supply of the prescribed drug, may make an observation, may count out a prescribed quantity of drugs and place them into a prescription container, etc. Some portions of the manual fulfillment process may be automated by use of a machine. For example, counting of capsules, tablets, or pills may be at least partially automated (such as through use of a pill counter). Prescription drugs dispensed by the manual fulfillment device 216 may be packaged individually or collectively for shipping, or may be shipped in combination with other prescription drugs dispensed by other devices in the high-volume fulfillment center.

The review device 218 may process prescription containers to be reviewed by a pharmacist for proper pill count, exception handling, prescription verification, etc. Fulfilled prescriptions may be manually reviewed and/or verified by a pharmacist, as may be required by state or local law. A pharmacist or other licensed pharmacy person who may dispense certain drugs in compliance with local and/or other laws may operate the review device 218 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been canceled, containers with defects, etc. In an example, the manual review can be performed at a manual review station.

The imaging device 220 may image containers once they have been filled with pharmaceuticals. The imaging device 220 may measure a fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 114 and/or stored in the storage device 110 as part of the order data 118.

The cap device 222 may be used to cap or otherwise seal a prescription container. In some implementations, the cap device 222 may secure a prescription container with a type of cap in accordance with a user preference (e.g., a preference regarding child resistance, etc.), a plan sponsor preference, a prescriber preference, etc. The cap device 222 may also etch a message into the cap, although this process may be performed by a subsequent device in the high-volume fulfillment center.

The accumulation device 224 accumulates various containers of prescription drugs in a prescription order. The accumulation device 224 may accumulate prescription containers from various devices or areas of the pharmacy. For example, the accumulation device 224 may accumulate prescription containers from the unit of use device 212, the automated dispensing device 214, the manual fulfillment device 216, and the review device 218. The accumulation device 224 may be used to group the prescription containers prior to shipment to the member.

The literature device 228 prints, or otherwise generates, literature to include with each prescription drug order. The literature may be printed on multiple sheets of substrates, such as paper, coated paper, printable polymers, or combinations of the above substrates. The literature printed by the literature device 228 may include information required to accompany the prescription drugs included in a prescription order, other information related to prescription drugs in the order, financial information associated with the order (for example, an invoice or an account statement), etc.

In some implementations, the literature device 228 folds or otherwise prepares the literature for inclusion with a prescription drug order (e.g., in a shipping container). In other implementations, the literature device 228 prints the literature and is separate from another device that prepares the printed literature for inclusion with a prescription order.

The packing device 226 packages the prescription order in preparation for shipping the order. The packing device 226 may box, bag, or otherwise package the fulfilled prescription order for delivery. The packing device 226 may further place inserts (e.g., literature or other papers, etc.) into the packaging received from the literature device 228. For example, bulk prescription orders may be shipped in a box, while other prescription orders may be shipped in a bag, which may be a wrap seal bag.

The packing device 226 may label the box or bag with an address and a recipient's name. The label may be printed and affixed to the bag or box, be printed directly onto the bag or box, or otherwise associated with the bag or box. The packing device 226 may sort the box or bag for mailing in an efficient manner (e.g., sort by delivery address, etc.). The packing device 226 may include ice or temperature sensitive elements for prescriptions that are to be kept within a temperature range during shipping (for example, this may be necessary in order to retain efficacy). The ultimate package may then be shipped through postal mail, through a mail order delivery service that ships via ground and/or air (e.g., UPS, FEDEX, or DHL, etc.), through a delivery service, through a locker box at a shipping site (e.g., AMAZON locker or a PO Box, etc.), or otherwise.

The unit of use packing device 230 packages a unit of use prescription order in preparation for shipping the order. The unit of use packing device 230 may include manual scanning of containers to be bagged for shipping to verify each container in the order. In an example implementation, the manual scanning may be performed at a manual scanning station. The pharmacy fulfillment device 112 may also include a mail manifest device 232 to print mailing labels used by the packing device 226 and may print shipping manifests and packing lists.

While the pharmacy fulfillment device 112 in FIG. 2 is shown to include single devices 206-232, multiple devices may be used. When multiple devices are present, the multiple devices may be of the same device type or models, or may be a different device type or model. The types of devices 206-232 shown in FIG. 2 are example devices. In other configurations of the system 100, lesser, additional, or different types of devices may be included.

Moreover, multiple devices may share processing and/or memory resources. The devices 206-232 may be located in the same area or in different locations. For example, the devices 206-232 may be located in a building or set of adjoining buildings. The devices 206-232 may be interconnected (such as by conveyors), networked, and/or otherwise in contact with one another or integrated with one another (e.g., at the high-volume fulfillment center, etc.). In addition, the functionality of a device may be split among a number of discrete devices and/or combined with other devices.

Figure 3:
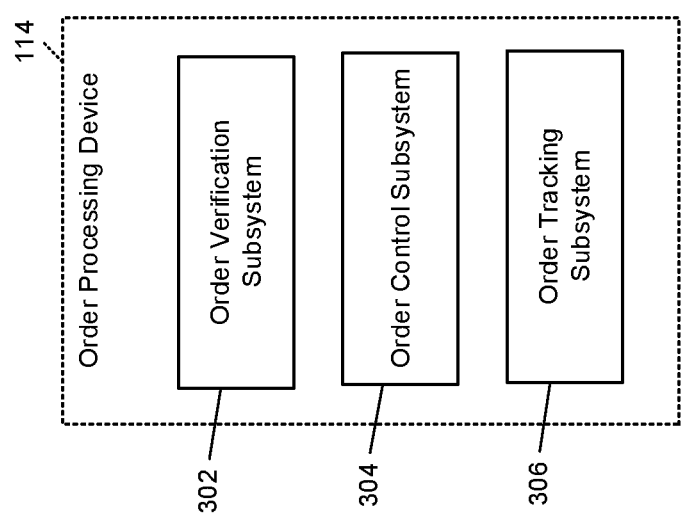
FIG. 3 is a functional block diagram of an example order processing device, which may be deployed within the system of FIG. 1.

FIG. 3 illustrates the order processing device 114 according to an example implementation. The order processing device 114 may be used by one or more operators to generate prescription orders, make routing decisions, make prescription order consolidation decisions, track literature with the system 100, and/or view order status and other order related information. For example, the prescription order may be comprised of order components.

The order processing device 114 may receive instructions to fulfill an order without operator intervention. An order component may include a prescription drug fulfilled by use of a container through the system 100. The order processing device 114 may include an order verification subsystem 302, an order control subsystem 304, and/or an order tracking subsystem 306. Other subsystems may also be included in the order processing device 114.

The order verification subsystem 302 may communicate with the benefit manager device 102 to verify the eligibility of the member and review the formulary to determine appropriate copayment, coinsurance, and deductible for the prescription drug and/or perform a DUR (drug utilization review). Other communications between the order verification subsystem 302 and the benefit manager device 102 may be performed for a variety of purposes.

The order control subsystem 304 controls various movements of the containers and/or pallets along with various filling functions during their progression through the system 100. In some implementations, the order control subsystem 304 may identify the prescribed drug in one or more than one prescription orders as capable of being fulfilled by the automated dispensing device 214. The order control subsystem 304 may determine which prescriptions are to be launched and may determine that a pallet of automated-fill containers is to be launched.

The order control subsystem 304 may determine that an automated-fill prescription of a specific pharmaceutical is to be launched and may examine a queue of orders awaiting fulfillment for other prescription orders, which will be filled with the same pharmaceutical. The order control subsystem 304 may then launch orders with similar automated-fill pharmaceutical needs together in a pallet to the automated dispensing device 214. As the devices 206-232 may be interconnected by a system of conveyors or other container movement systems, the order control subsystem 304 may control various conveyors: for example, to deliver the pallet from the loading device 208 to the manual fulfillment device 216 from the literature device 228, paperwork as needed to fill the prescription.

The order tracking subsystem 306 may track a prescription order during its progress toward fulfillment. The order tracking subsystem 306 may track, record, and/or update order history, order status, etc. The order tracking subsystem 306 may store data locally (for example, in a memory) or as a portion of the order data 118 stored in the storage device 110.

Per-User Determination Controller

Figure 4:
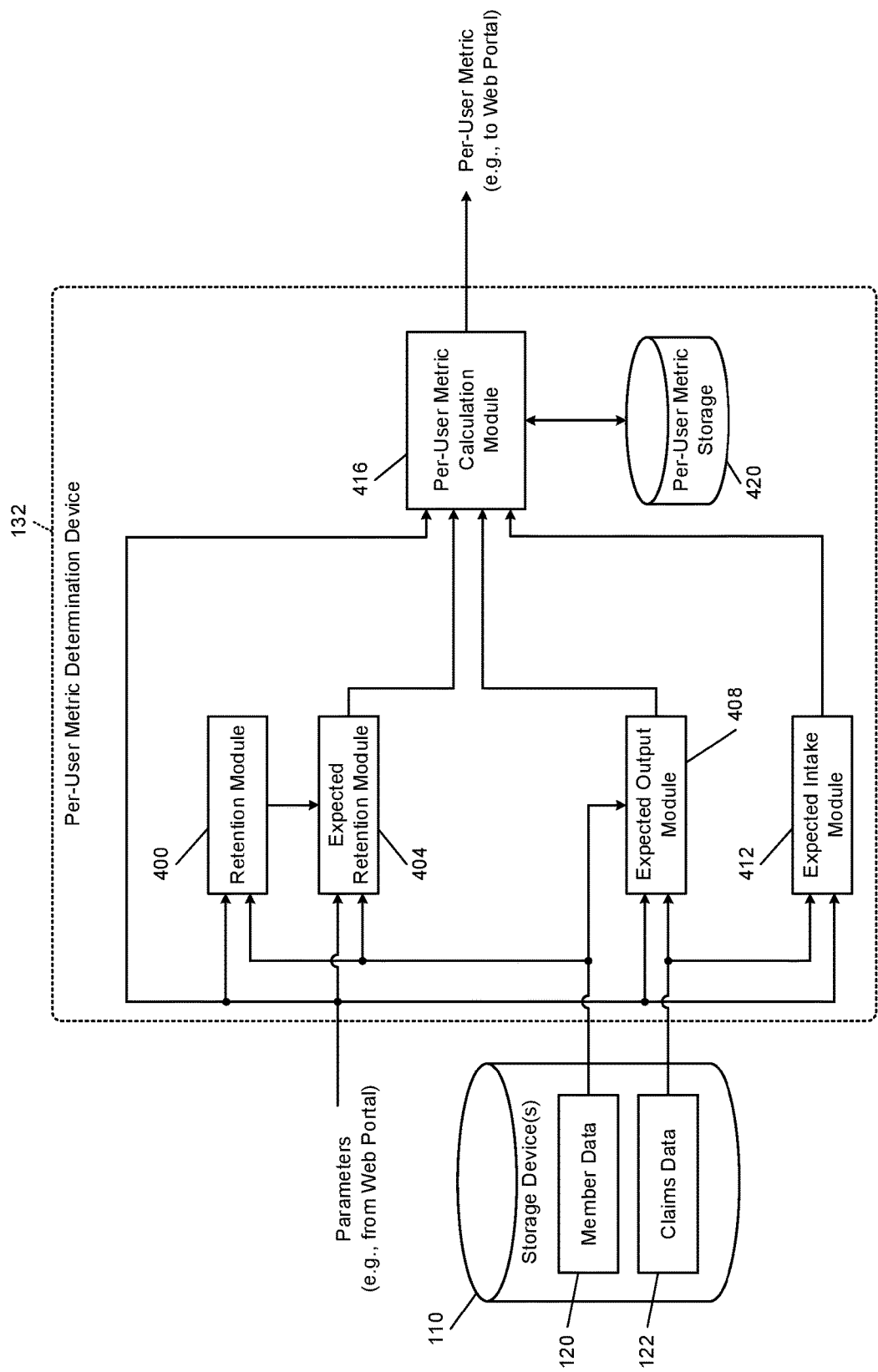
FIG. 4 is a functional block diagram of an example per-user metric determination device.

FIG. 4 is a functional block diagram of an example per-user metric determination device 132. The per-user metric determination device 132 receives input parameters and accesses member data 120 and claims data 122 from the storage device 110 to calculate a per-user metric of a user, depending on the input parameters. While the present application refers to the per-user metric of the user, a population-wide metric of the user population may also be determined using the per-user metric determination device 132.

In various implementations, for each per-user metric calculation, the per-user metric determination device 132 may identify multiple processing threads on each of multiple processor cores and assign calculations of the per-user metric calculation to respective threads. To calculate the per-user metric, a retention module 400 receives input parameters. For example, when a selected user logs into their account, the retention module 400 may receive input parameters from an account of the selected user. In such an implementation, the user identity may be received in response to the selected user logging into their account. In various implementations, the input parameters include the user identity and the current user population. While using an analyst device, an analyst may input the user identity along with the user population). The user population may indicate demographic data or employment information of the selected user. For example, the employees of the selected user's employer may form the user population.

The retention module 400 calculates the amount of time the user and the user population was retained as a patient of the organization during a time period—for example, the prior year based on the user account information and user duration data maintained in the member data 120. In various implementations, the retention module 400 receives member data 120 from the storage device 110 to obtain duration data for each member of the user population.

The per-user metric determination device 132 also includes an expected retention module 404. The expected retention module 404 receives the input parameters, the member data 120, and the actual user/population retention calculated by the retention module 400. The expected retention module 404 identifies relevant demographic data in the member data 120. The relevant demographic data may include the age of the user and employment information of the user. The expected retention module 404 can compare the user's age, employment information, and actual historical retention to historical retention rates of users in similar circumstances.

In various implementations, similar circumstances may be determined from demographic data and may include an age range, employer, etc. The historical retention rates of users in similar circumstances may be determined from data included in the member data 120. The expected retention module 404 calculates the expected user retention and the expected population retention that includes the selected user based on historical retention rates of the selected user, the population of the selected user, and retention of users in similar circumstances. For example, if users in an age range of 20-25 years have an actual historical retention rate of 80%, the expected retention module 404 may determine the same expected retention rate of 80% for a 23-year-old user when comparing the 23-year-old user to users in the respective age range.

An expected output module 408 receives member data 120 and claims data 122 as well as the input parameters. In various implementations, the expected output module 408 also receives historical claims data of a selected training group of approved members in the claims data 122. Members are identified as approved members if the member data (as well as other data corresponding to the member) is allowed to be included in data processing and modeling. For example, certain members may be excluded from data processing and modeling based on restrictions on the use of their healthcare information.

The selected training group, for example, may include historical claims of 500,000 approved users for a previous time period, such as the prior year. The expected output module 408 obtains behavioral data for each user in the training group from the member data 120. For example, the expected output module 408 identifies a number of times each user in the training group has called a support center of the pharmacy per claim used any other resource of the pharmacy (such as requesting shipment of drugs) over the previous period of time. The expected output module 408 quantifies each use to determine a previous output of each user in the training group. The previous output of each user in the training group indicates an output or cost required to serve the respective user in the training group. The output may include all costs incurred to serve the user.

Similarly, the expected output module 408 determines previous outputs of each user of the training group during the previous period of time. In various implementations, an output model of the training group is included in the expected output module 408. The output model is a trained machine learning model that predicts future output: for example, for the next year. The training group is used to train the output model and a test group for example, of the same size or smaller than the training group is used to verify the accuracy of the output model. The expected output module 408 determines an expected output of the user based on the output model and previous user output over a future time period, where the future time period is an input parameter. For example, the future time period for the web portal may be a predetermined value, such as one year. Meanwhile, an analyst may choose the future time period according to their analytical task.

The per-user metric determination device 132 also includes an expected intake module 412. The expected intake module 412 indicates an amount received by the pharmacy based on the claims the user has made over the previous time period. The expected intake module 412 receives member data 120 and claims data 122 as well as the input parameters. In various implementations, the expected output module 408 and the expected intake module 412 are included in one module. Similar to the expected output module 408, the expected intake module 412 includes an intake model created according to a machine learning method. The intake model is a trained model that predicts future intake: for example, for the next year. In various implementations, the intake represents margin or resources received from a user for an event: for example, an amount paid by the user and/or another payer (such as a health plan) for receiving a drug. In various implementations, the intake may represent the amount the user paid for the drug less the amount the pharmacy expended to procure, handle, store, and ship the drug.

The output model and the intake model are trained on a regular basis instead of being trained each time a metric is calculated. The intake model is created from historical claims data and extracts claims to analyze the intake from each claim for each user over the previous time period. Based on the input parameters, the expected intake module 412 determines an expected intake of the user based on the intake model and previous user intake over a future time period, where the future time period is an input parameter.

The expected retention module 404, the expected output module 408, and the expected intake module 412 may all include machine learning models generated by a data processing circuit. For example, the data processing circuit may be included in the per-user metric determination device 132 or within each of the previously listed modules. To generate the respective models, a set of users is identified. A machine learning model is trained based on event data of the set of identified users over a predetermined previous period or epoch for example, the previous year. The machine learning model for the respective modules can identify relevant information included in the event data. For example, a model generated for or by the expected output module 408 may identify information regarding an output of each event to train the model based on previous output received for the set of identified users over the predetermined previous period.

As previously mentioned, in various implementations, the machine learning model may be trained using parallel processing for records obtained from the storage device 110. The parallel processing includes assigning the analysis of the stored event data for each set of identified users to respective processor threads for parallel execution on processing hardware. Using parallel processing to train the models described above is a new and efficient method to train models faster.

A per-user metric calculation module 416 receives the input parameters, the expected user retention and the expected population retention from the expected retention module 404, the expected output of the user from the expected output module 408, and the expected intake of the user from the expected intake module 412. The per-user metric calculation module 416 calculates a per-user metric of the user based on the received information. In various implementations, the per-user metric calculation module 416 calculates the per-user metric according to the following equation:

$$PUM_k = A_k \sum_{i=1}^{n} \frac{G_i(M_k - C_k)r^i}{(1+d)^i}$$

where $PUM_k$ is the per-user metric of the user identified by an integer identifier k, $A_k$ is the starting retention age of the user, n is the number of future years to consider, $G_i$ is the drop in user retention at the future year i based on the expected user retention, $M_k$ is the expected intake of the user, $C_k$ is the expected output of the user, r is the expected population retention rate of the user population, and d is a discount rate that a user or user population may receive. The per-user metric is output to the requesting device, such as the web portal.

The per-user metric determination device 132 also includes a per-user metric storage 420. The per-user metric storage 420 can be accessed via the per-user metric calculation module 416. If the per-user metric of the user has already been calculated, the per-user metric calculation module 416 may retrieve the per-user metric of the user from the per-user metric storage 420. Each time a per-user metric is calculated, the per-user metric may be stored in the per-user metric storage 420.

In various implementations, the per-user metric determination device 132 can determine the per-user metric of the user during a previous time. That is, the input parameters may specify a retrospective time period. The per-user metric determination device 132 will access historical data included in the storage device 110 of the corresponding user. In this way, a comparison may be made between the per-user metric of the user during the previous time and the current per-user metric of the user.

In various implementations, the per-user metric determination device 132 may be an interface circuit capable of performing all the functions of the per-user metric determination device 132 described above. Similarly, the per-user metric may be described as an interface metric.

Flowcharts

Figure 5:
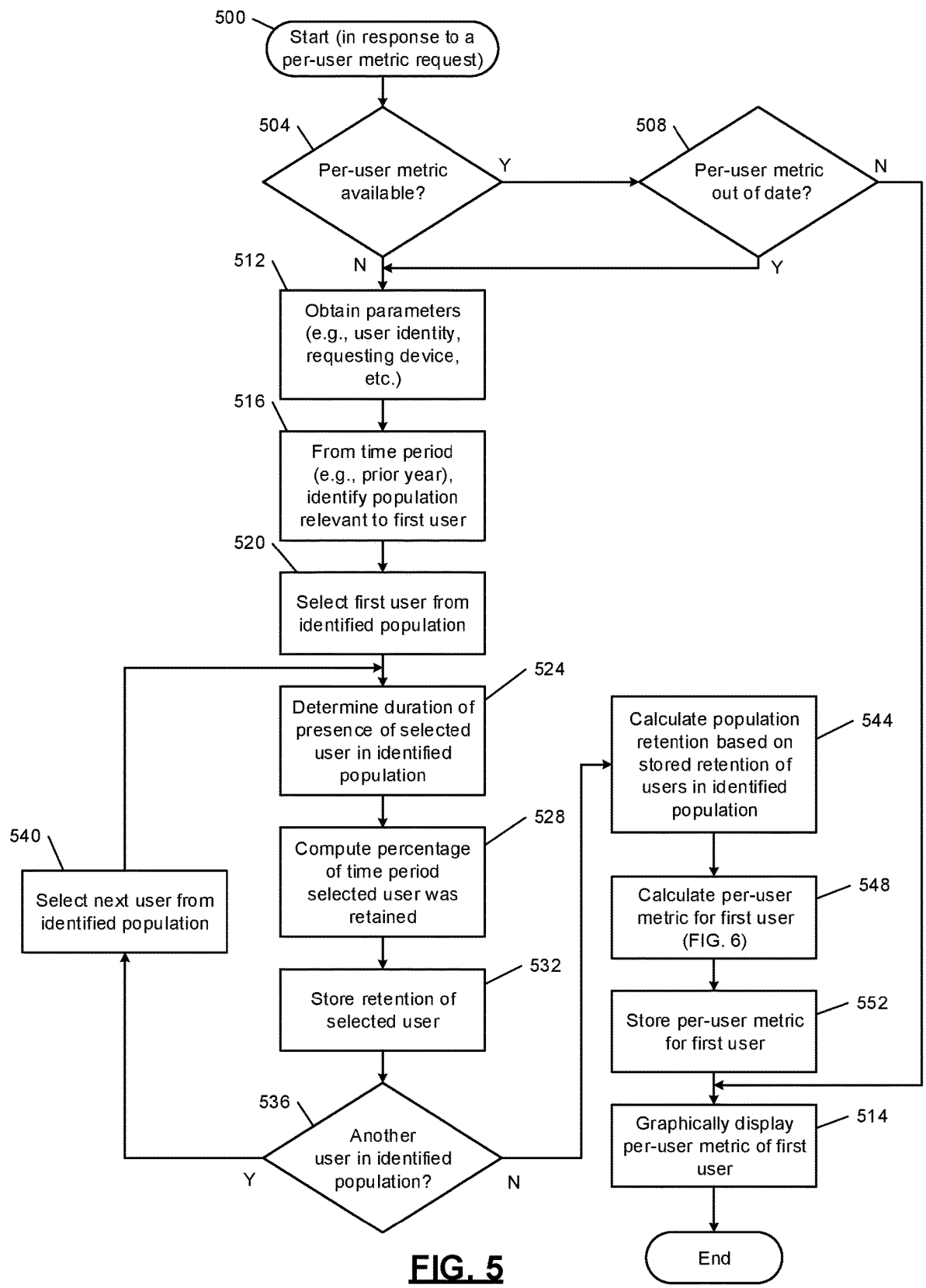
FIG. 5 is a flowchart of an example per-user metric being determined.

FIG. 5 is a flowchart of example determination of a per-user metric request. Control begins at 500 in response to a per-user metric request. Once the request is received, control continues to 504 where control determines if the per-user metric is available. For example, if the per-user metric was previously calculated and stored in an accessible storage, then the per-user metric is available. If the per-user metric is available, control continues to 508; otherwise, control continues to 512. At 508, control determines whether the per-user metric is out of date. If so, control transfers to 514; otherwise, control transfers to 512.

At 512, control obtains input parameters. For example, input parameters may include a user identity, the requesting device (the web portal, the support device, the analyst device, etc.), a discount rate of the user, etc. Control then continues to 516 where the relevant population of the user is identified from a time period, for example, a prior year.

Once the population relevant to the user is identified, control continues to 520, where the first user is selected from the identified population. Control proceeds to 524, where a duration of presence of the selected user in the identified population is determined. Control then continues to 528 to compute a percentage of the time period that the selected user was retained. That is, control calculates the amount of time the selected user was included in the identified population during the time period. In this way, the amount of time the user was retained in the identified population during the time period is calculated.

Control continues to 532 to store the completed retention of the selected user. Control proceeds to 536 to determine if another user is included in the identified population. If so, control proceeds to 540 where the next user of the identified population is selected. Control then returns to 524 to determine the duration of presence of the selected user in the identified population. If, at 536, there are no additional users to evaluate in the identified population, control continues to 544, where control calculates the population retention based on the stored retention of users in the identified population. In this way, individual retention rates are calculated along with the retention rate of the entire population.

Figure 6:
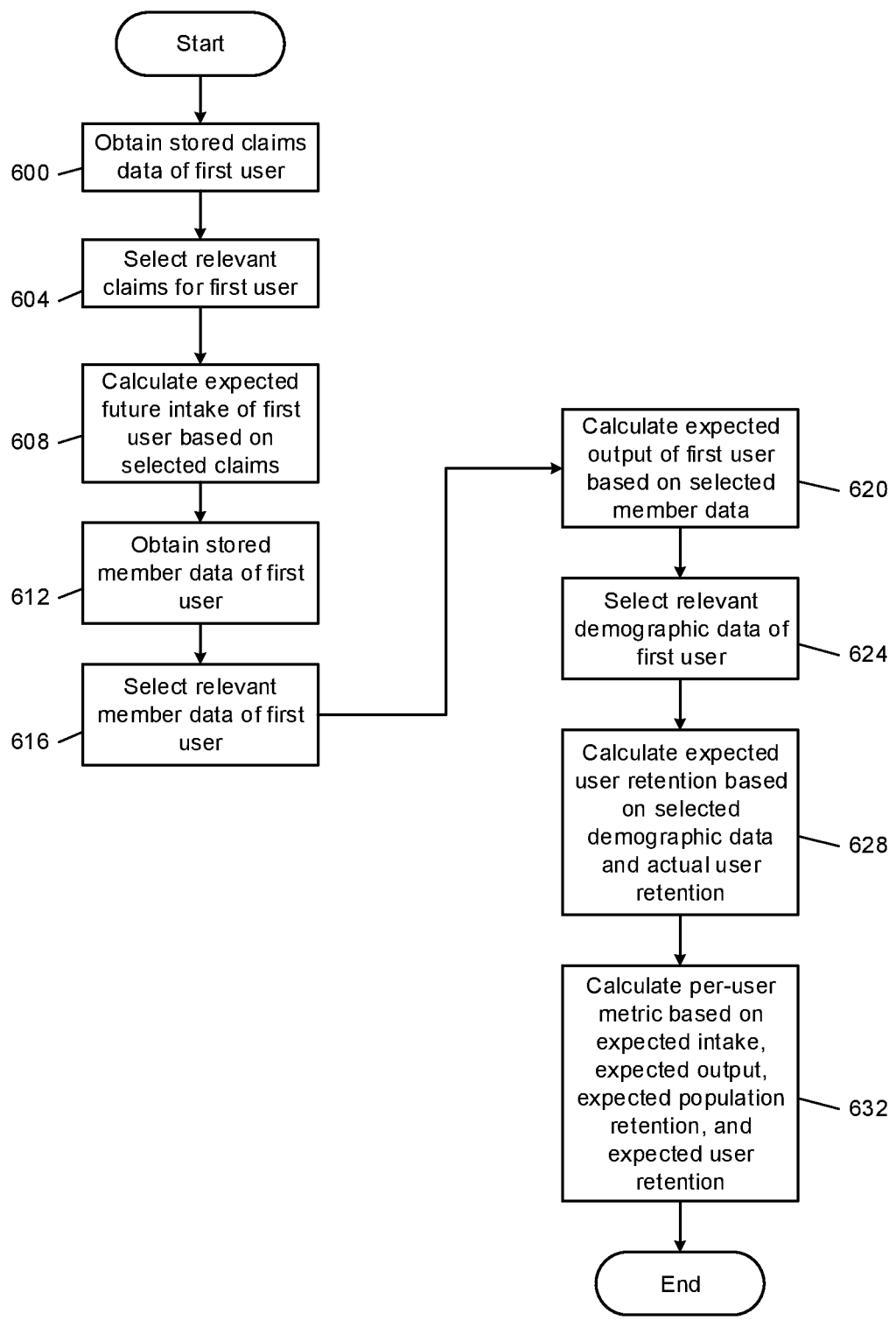
FIG. 6 is a flowchart of an example per-user metric calculation.

Control proceeds to 548 where control calculates the per-user metric for the first user. FIG. 6 describes an example of per-user metric calculation. Once calculated, the per-user metric for the first user is stored at 552. Control proceeds to 514 where the per-user metric of the first user is graphically displayed and control ends. In various implementations, the analyst device described in FIG. 1 calculates the per-user metric and displays the per-user metric along with a transformed user interface for the persona corresponding to the per-user metric.

FIG. 6 is a flowchart of an example per-user metric calculation. Control begins at 600, where the stored claims data of the first user is obtained. Control continues to 604 where relevant claims for the first user are selected from the claims data. At 608, control calculates the expected intake of the first user based on the selected claims. Then at 612, control obtains stored member data of the first user, such as from a storage device. Control proceeds to 616, where relevant member data of the first user is selected. At 620, control calculates an expected output of the first user based on the selected member data.

Then, at 624, control selects relevant demographic data of the first user from the member data. Control continues to 628, where expected user retention is calculated based on the selected demographic data and actual user retention. For example, the actual user retention may be calculated as shown in FIG. 5. At 632, control calculates the per-user metric of the first user based on the expected intake, the expected output, the expected population retention, and the expected user retention of the first user.

Figure 7:
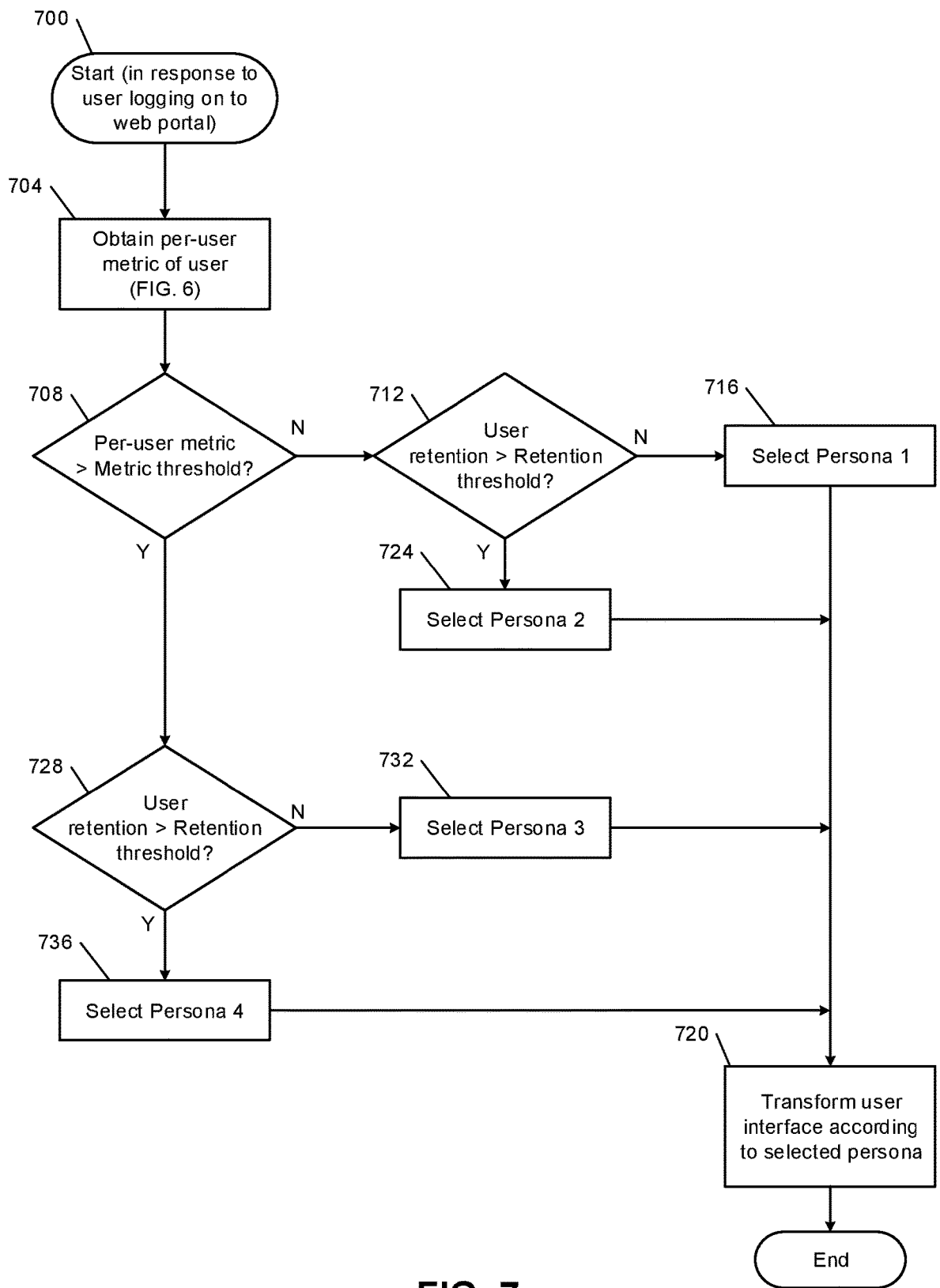
FIG. 7 is a flowchart of an example persona selection for a web portal.

FIG. 7 is a flowchart of an example persona selection for a web portal. Control begins at 700, in response to a user logging on to the web portal. Once a user has logged on to the web portal, control proceeds to 704 and obtains the per-user metric of the logged-on user, as described in FIG. 6. Control then continues to 708 to determine if the per-user metric is greater than a metric threshold. If not, control proceeds to 712 to determine if a user retention is greater than a retention threshold. In various implementations, the user retention may be a measure of actual user retention over the prior year. As another example, the user retention may be an expected user retention for the upcoming year. If the user retention is not greater than the retention threshold, control continues to 716 and selects persona 1. Persona 1 represents a user with a low per-user metric as well as a low retention. When the user corresponds to persona 1, the user interface will be modified to encourage the user to achieve a higher per-user metric and/or higher user retention. The user interface may also be modified to remove higher-overhead items, such as free expedited shipping, for the user whose retention is unlikely to be affected by such perks. Once persona 1 is selected at 716, control continues to 720 to transform the user interface on the web portal to correspond to the identified persona, and control ends.

Returning to 712, if the user retention is greater than the retention threshold, control continues to 724 and selects persona 2. Persona 2 represents a user with a low per-user metric and a high user retention. When the user corresponds to persona 2, the user interface will be modified to encourage the user to achieve a higher per-user metric and may offer benefits based on the high user retention. Once persona 2 is selected, control continues to 720.

Returning to 708, if the per-user metric is greater than the metric threshold, control continues to 728. At 728, control determines if the user retention is greater than a retention threshold. If not, control continues to 732 and selects persona 3. Persona 3 represents a user with a high per-user metric but a low user retention. Similar to persona 2, the user interface will be modified to encourage the user to achieve higher user retention but may provide or suggest certain benefits based on the high per-user metric. Once persona 3 is selected, control continues to 724.

Returning to 728, if the user retention is greater than the retention threshold, control continues to 736 and selects persona 4. Persona 4 represents a user with a high per-user metric as well as a high user retention. Therefore, the user interface may offer certain benefits to the user based on the high per-user metric and high user retention. Once persona 4 is selected, control continues to 724.

In various implementations, the user interface options for each persona include two variations of the user interface that are displayed to users. The users for each persona will be categorized into two groups. A first variation of a corresponding persona will be displayed to a first group and a second variation of the corresponding persona will be displayed to a second group. In various implementations, users are assigned to each group randomly. The per-user metric of each user of each group will be monitored over a testing period for example, one month. At the end of the testing period, the per-user metric of each user at the end of the testing period is compared to the per-user metric of each user at the beginning of the testing period. Then, the average per-user metric of the first group is compared to the average per-user metric of the second group at the beginning and end of the testing period. The variation that corresponds to the group that has the most improved averaged per-user metric by the end of the testing period is selected and used for all users of the corresponding persona.

Figure 8:
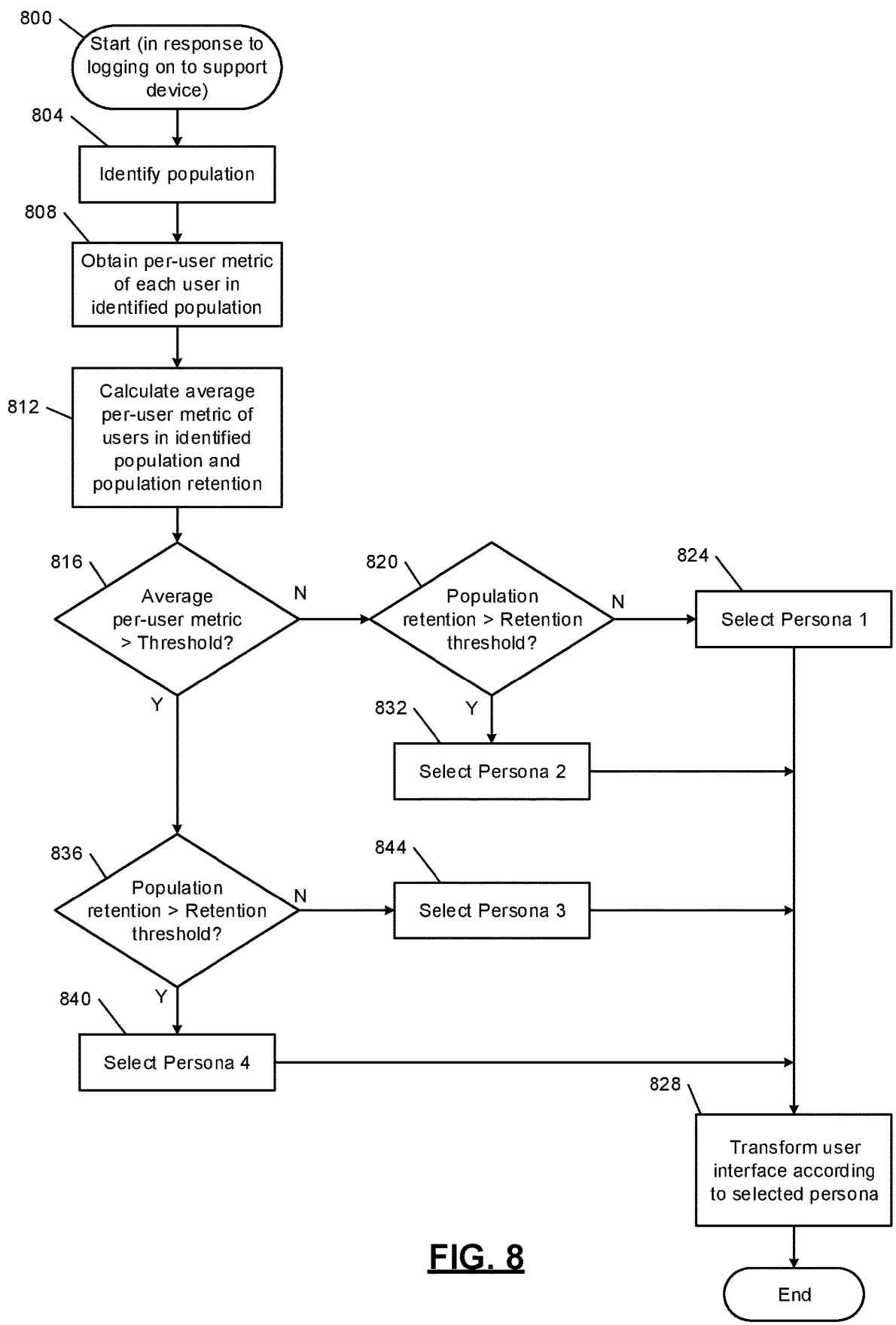
FIG. 8 is a flowchart of an example persona selection for a support device.

FIG. 8 is a flowchart of an example persona selection for a support device. Control begins at 800, in response to a support representative logging onto the support device. As mentioned previously, the present disclosure applies to calculating a per-user metric as well as a population metric. For purposes of FIG. 8, the flowchart will describe calculating an average metric of the population. However, on average FIG. 8 may instead be implemented with an individual per-user metric and a population retention value.

Once the support representative has logged on to the support device, control continues to 804 and identifies a population. For example, the support representative may have received a phone call and while conducting the phone call the support representative may input the identity of the user that is calling. The population is then identified based on the user identity, such as the prescription plan to which the user belongs. Control continues to 808 to obtain a per-user metric of each user in the identified population. For example, FIG. 5 describes calculating population retention, and FIG. 6 describes how to calculate a per-user metric of a particular user.

Control then continues to 812 to calculate the average per-user metric of users in the identified population and the population retention. Once the average is calculated, control continues to 816 to determine if the average per-user metric is greater than a metric threshold. If not, control continues to 822 determine if the population retention of the identified population is greater than a retention threshold. If not, control continues to 824 and selects persona 1.

Control continues to 828, where the user interface on the support device is transformed according to the identified persona, and control ends. When a persona is being determined for the support device, the personas may be different from the personas selected for the web portal. For example, when the identified population has a low average per-user metric and a low retention that is, when control selects persona one the user interface of the support device may display fewer benefit options for the support representative to offer the identified population. Further, for every persona, the support device may display the average per-user metric of the identified population as well as the population retention to inform the support representative of these metrics. Additionally, when the persona indicates a higher average per-user metric or a higher retention likelihood (such as persona 4), the user interface of the support device may offer more benefit options for the support representative to offer the user.

Returning to 820, if the population retention is greater than the retention threshold, then control continues to 832 and selects persona 2. Control then continues to 828. Returning to 816, if the average per-user metric is greater than the metric threshold, then control continues to 836. At 836, control determines if the population retention is greater than the retention threshold. If so, control continues to 840, selects persona 4, and continues to 828. Otherwise, control continues to 844, selects persona 3, and continues to 828.

User Interface

Figure 9B:
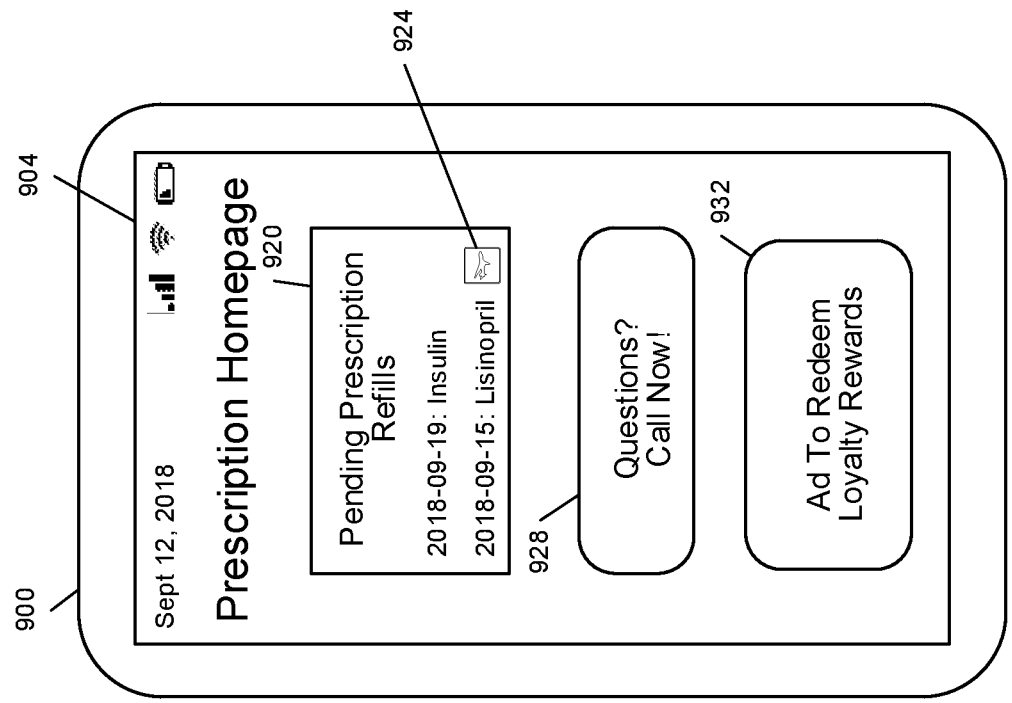
FIG. 9B is an example user interface adaptation of a prescription interface for a high per-user metric.
Figure 9A:
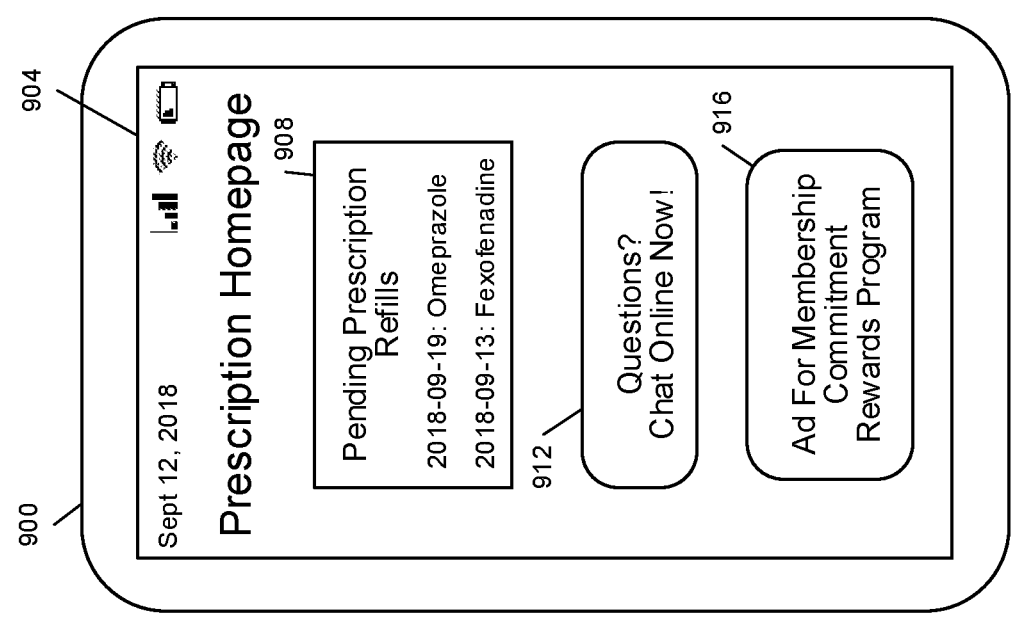
FIG. 9A is an example user interface adaptation of a prescription interface for a low per-user metric.

FIG. 9A is an example user interface adaptation of a prescription interface, such as a homepage or application screen for a low per-user metric. In various implementations, a user accesses the prescription interface using a user device 900. The user device 900 may be a desktop computer, kiosk, or mobile computing device, such as a phone or tablet. The user device 900 includes a display screen 904, which displays the prescription interface. In various implementations, when a user has a low per-user metric as well as a low user retention (personal), the user interface of the prescription interface will provide encouragement for the user to increase their per-user metric as well as their retention likelihood.

For example, the prescription interface may include a pending prescription refills area 908 that includes a list of pending refills. The prescription interface may also include an advertisement for online chatting with support representatives 912. For example, as shown the advertisement may read "Questions? Chat Online Now!" The prescription interface may also include a membership advertisement 916. The membership advertisement 916 may be a rewards program based on user commitment, such as automatic refills of prescriptions.

In various implementations, each of the user interface adaptation modules 130-2, 134-2, and 136-2 of FIG. 1 are configured to perform a modification of a user interface element on the user interface of the respective device based on the per-user metric. For example, as shown in FIG. 9A, the prescription interface may include a pending prescription refills area 908 that includes a list of pending refills. The prescription interface may also include an advertisement for online chatting with support representatives 912. For example, as shown the advertisement may read "Questions? Chat Online Now!" The prescription interface may also include a membership advertisement 916. The membership advertisement 916 may be a rewards program based on user commitment, such as automatic refills of prescriptions. The modification of the instant user interface may be altering the online chat advertisement to offer the option of calling a support representative in response to the per-user metric of the user. Alternatively, in various implementations, the advertisement user interface element may be removed from the user interface.

FIG. 9B is an example user interface adaptation of a prescription interface for a user with a high per-user metric. The display screen 904 of the user device 900 will display a different user interface for users that have a higher per-user metric as well as a higher user retention likelihood, as shown in FIG. 9B. For example, a pending prescription refills area 920 may include a list of pending refills. In various implementations, for certain upcoming prescription refills, an expedite shipping button 924 may appear if the pending prescription refill date is quickly approaching. Further, for the user with a higher per-user metric, an advertisement for the user to call, rather than simply chat with, a support representative 928 may appear on the prescription interface. For example, the advertisement may read "Questions? Call Now!" Additionally, an advertisement to redeem loyalty rewards 932 may also appear based on the user's commitment to the pharmacy.

CONCLUSION

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A. The term subset does not necessarily require a proper subset. In other words, a first subset of a first set may be coextensive with (equal to) the first set.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4.

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules.

References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PUP: Hypertext Preprocessor), Scala, Eiffel, Smalltalk, Erlang, Ruby, Flash®, Visual Basic®, Lua, MATLAB, SIMULINK, and Python®.

What is claimed is:

1. A computer system for dynamic adaptation of a user interface according to data store mining, the computer system comprising:
a data store configured to index event data of a plurality of events, wherein each event of the plurality of events corresponds to a physical object being supplied to a user identified by an identifier on behalf of a first entity, wherein the data store is configured to store descriptive data for each of a plurality of identifiers;
a data analyst device configured to render the user interface to a data analyst and to transmit a message that identifies a selected identifier of the plurality of identifiers, wherein the user interface includes a first user interface element and a second user interface element;
a data processing circuit configured to:
identify a first set of identifiers from the plurality of identifiers based on commonality among the descriptive data stored by the data store across the first set of identifiers; and
train a machine learning model for the first set of identifiers based on event data stored by the data store for the first set of identifiers from within a predetermined epoch,
wherein the machine learning model is trained using parallel processing of records from the data store, wherein the parallel processing includes assigning analysis of the indexed event data of each of a subset of the first set of identifiers to respective processor threads for parallel execution on processing hardware; and
an interface circuit configured to, in response to receiving the message from the data analyst device:
determine an output of the selected identifier using the machine learning model from the data processing circuit, wherein the output of the selected identifier represents an amount of resources expected to be used by the selected identifier for a second epoch subsequent to the predetermined epoch;
determine an interface metric for the selected identifier based on the determined output of the selected identifier; and
transmit the interface metric to the data analyst device,
wherein the data analyst device is configured to, in response to the interface metric from the interface circuit, selectively perform at least one of modification and removal of the second user interface element.

2. The system of claim 1 wherein the interface circuit is configured to determine the interface metric for the selected identifier further based on:
a retention value, wherein the retention value indicates a likelihood of the selected identifier being associated with the first entity for the second epoch; and
a population retention value, wherein the population retention value indicates a likelihood of a population of identifiers encompassing the selected identifier being associated with the first entity for the second epoch.

3. The system of claim 1 wherein an operator of the data analyst device is one of (i) a user identified by the selected identifier, (ii) an analyst for the first entity, and (iii) a support representative of the first entity.

4. The system of claim 1 wherein the amount of resources expected to be used by the selected identifier includes at least one of: (i) an expected number of calls received from the selected identifier, (ii) an expected number of drug orders mailed to the selected identifier; and (iii) an expected measure of drugs dispensed to the selected identifier.

5. The system of claim 1 wherein the interface circuit is configured to, in response to receiving the message from the data analyst device:
determine an intake of the selected identifier using a machine learning model from the data processing circuit, wherein the intake of the selected identifier represents an amount of resources expected to be received by the first entity from the selected identifier for the second epoch; and determine the interface metric for the selected identifier based on the determined output of the selected identifier and the determined intake of the selected identifier.

6. The system of claim 5 wherein the amount of resources expected to be received from the selected identifier is a difference, for each event of the selected identifier, between an amount received for the event and an amount expended for the event.

7. The system of claim 1 wherein the data analyst device includes a persona determination module configured to:
transmit the message to the interface circuit;
receive the interface metric of the selected identifier from the interface circuit; and
identify a corresponding persona of the selected identifier based on the received interface metric of the selected identifier.

8. The system of claim 7 wherein the data analyst device includes a user interface adaptation module configured to transform the user interface of the data analyst device according to the corresponding persona.

9. The system of claim 7 wherein the corresponding persona is selected from a set of personas including at least one of: (i) a set of user personas, (ii) a set of analyst personas; and (iii) a set of support personas.

10. The system of claim 1 wherein the selected identifier is a population of identifiers encompassing the selected identifier.

11. The system of claim 1 wherein descriptive data for each of the plurality of identifiers includes at least one of: (i) name, (ii) support call logs, (iii) support chat logs, and (iv) selected identifier subscription duration.

12. The system of claim 1 wherein descriptive data for each of the plurality of identifiers includes population of identifiers encompassing the selected identifier subscription duration.

13. The system of claim 1 wherein the event data includes at least one of, for each event: (i) a respective intake and (ii) a respective output.

14. The system of claim 1 wherein the interface circuit includes a retention module configured to:
identify a population of identifiers encompassing the selected identifier;

determine a previous retention value of the selected identifier based on a duration of presence of the selected identifier within the identified population during the predetermined epoch; and determine a previous population retention value of the identified population based on a duration of presence of the identified population as a client of the first entity during the predetermined epoch.

15. The system of claim 14 wherein:
the interface circuit calculates the interface metric according to an equation;
the equation is:

$$PUM_k = A_k \sum_{i=1}^{n} \frac{G_i(M_k - C_k)r^i}{(1+d)^i};$$

$PUM_k$ is the interface metric of the selected identifier;
$A_k$ is a starting retention age of the selected identifier;
n is a length of the second epoch in years;
$G_i$ is an estimate of a retention value of the selected identifier at year i of the second epoch;
$M_k$ is an estimated intake of the selected identifier for the second epoch;
$C_k$ is the determined output of the selected identifier;
r is an annual population retention value; and
d is a predetermined discount rate.

16. The system of claim 15 wherein:
the length of the second epoch in years is an integer greater than or equal to one;
the estimate of the retention value is less than or equal to zero;
the annual population retention value is less than or equal to one; and the predetermined discount rate is greater than or equal to zero and less than one.

17. The system of claim 1 wherein the second user interface element indicates a shipping option of a drug.

18. The system of claim 17 wherein the at least one of modification and removal of the second user interface element includes, based on the interface metric, updating the shipping option of the drug to an expedited shipping option.

\* \* \* \* \*